(12) United States Patent
Kulkarni et al.

(10) Patent No.: US 7,256,216 B2
(45) Date of Patent: Aug. 14, 2007

(54) LIQUID PHARMACEUTICAL COMPOSITIONS

(75) Inventors: Neema M. Kulkarni, Randolph, NJ (US); Michael Schneider, Denzlingen (DE); Steven B. Silbering, Forest Hills, NY (US); Hans Meyer-Wonnay, Emmendingen (DE); Nahid Sanii-Yahyai, Ann Arbor, MI (US)

(73) Assignee: Warner-Lambert Company LLC

( * ) Notice: Subject to any disclaimer, the term of this patent is extended or adjusted under 35 U.S.C. 154(b) by 0 days.

(21) Appl. No.: 10/602,215

(22) Filed: Jun. 24, 2003

(65) Prior Publication Data

US 2004/0072904 A1    Apr. 15, 2004

Related U.S. Application Data

(63) Continuation of application No. 10/156,213, filed on May 28, 2002, now abandoned.

(60) Provisional application No. 60/343,733, filed on Oct. 25, 2001, provisional application No. 60/293,832, filed on May 25, 2001.

(51) Int. Cl.
*A61K 31/195* (2006.01)

(52) U.S. Cl. .................................... 514/561

(58) Field of Classification Search ............... 514/561, 514/738, 768
See application file for complete search history.

(56) References Cited

FOREIGN PATENT DOCUMENTS

| EP | 0652012 | 5/1995 |
|---|---|---|
| WO | 9959573 | 11/1999 |
| WO | 0243762 | 6/2002 |

OTHER PUBLICATIONS

Zour et al. Stability Studies of Gabapentin in Aqueous Solutions. Pharmaceutical Research, 1992, v. 9, pp. 595-600.*

* cited by examiner

*Primary Examiner*—Phyllis G. Spivack
*Assistant Examiner*—James D. Anderson
(74) *Attorney, Agent, or Firm*—Charles A. Ashbrook; Matthew J. Russo

(57) ABSTRACT

A liquid pharmaceutical composition of a GABA analog comprising at least one polyhydric alcohol containing 2 to 6 carbon atoms having a pH of about 5.5 to about 7.0 and additionally a two-component liquid pharmaceutical composition comprising a first component comprising a powder mixture comprising a GABA analog and a solid polyhydric alcohol, and a second component comprising a liquid base are described, as well as methods to prepare the compositions and a method for treating cerebral diseases, including epilepsy, faintness attacks, hypokinesia and cranial traumas, neurodegenerative disorders, depression, mania and bipolar disorders, anxiety, panic, inflammation, renal colic, insomnia, gastrointestinal damage, incontinence, pain, including neuropathic pain, muscular pain, skeletal pain, and migraine using a therapeutically effective amount of the pharmaceutical compositions.

8 Claims, No Drawings

LIQUID PHARMACEUTICAL COMPOSITIONS

This application is a continuation of U.S. application Ser. No. 10/156,213 filed May 28, 2002, now abandoned, which claims the benefit of U.S. Provisional Application 60/293,832 filed May 25, 2001, and U.S. Provisional Application 60/343,733 filed Oct. 25, 2001; the entire contents of each of which are hereby incorporated herein by reference.

FIELD OF THE INVENTION

This invention relates to liquid pharmaceutical compositions comprising a gamma-aminobutyric acid (GABA) analog and processes for the preparation of the same as well as methods of using such compositions to treat subjects, including human subjects, suffering from certain cerebral diseases, including epilepsy, faintness attacks, hypokinesia and cranial traumas, neurodegenerative disorders, depression, mania and bipolar disorders, anxiety, panic, inflammation, renal colic, insomnia, gastrointestinal damage, incontinence, pain, including neuropathic pain, muscular pain, skeletal pain, and migraine.

BACKGROUND OF THE INVENTION

GABA is an inhibitory amino acid found in the mammalian central nervous system (CNS). It has been reported that dysfunctions with GABA neurotransmission in the CNS may contribute or even cause psychiatric and neurological diseases such as epilepsy, schizophrenia, Parkinson's disease, Huntington's Chorea and dyskinesia (Saletu B., et al., *International Journal of Clinical Pharmacology, Therapy, and Toxicology*, 1986;24:362-373).

Gabapentin (1-(aminomethyl)-cyclohexaneocetic acid):

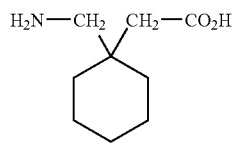

was designed as a GABA analog that would cross the blood-brain barrier. Gabapentin was found to have anticonvulsant and antispastic activity with extremely low toxicity in man. Gabapentin is presently marketed under the trademark Neurontin® as adjunctive therapy in the treatment of partial seizures in patients with epilepsy.

U.S. Pat. Nos. 4,024,175 and 4,087,544 disclose the use of gabapentin for the treatment of certain forms of epilepsy, faintness attacks, hypokinesia, and cranial traumas. Additionally, gabapentin brings about an improvement of cerebral functions and thus is useful in treating geriatric patients. U.S. Pat. No. 5,084,479 discloses the use of gabapentin in neurodegenerative disorders. U.S. Pat. No. 5,025,035 discloses the use of gabapentin in treating depression; U.S. Pat. No. 5,510,381 discloses the use of gabapentin in treating mania and bipolar disorders. U.S. Pat. No. 5,792,796 discloses the use of gabapentin in treating anxiety and panic. U.S. Pat. No. 6,127,418 discloses the use of gabapentin in treating gastrointestinal damage; U.S. Pat. Nos. 4,894,476 and 4,960,931 disclose a novel crystalline monohydrate form of gabapentin; and U.S. Pat. Nos. 5,133,451; 5,319,135; 5,362,883; 5,693,845; 5,091,567; and 5,068,413 disclose processes for preparing gabapentin as well as intermediates used in these processes. All of the aforementioned United States Patents are incorporated herein by reference.

Pregabalin ((S)-4-amino-3-(2-methylpropyl)butanoic acid)

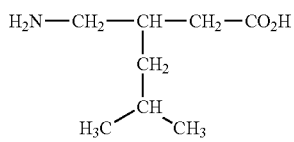

is another GABA analog disclosed in U.S. Pat. No. 5,563,175 for the treatment of seizure disorders including epilepsy, which is herein incorporated by reference.

U.S. Pat. No. 6,117,906 discloses the use of pregabalin in treating anxiety; U.S. Pat. No. 6,001,876 discloses the use of pregabalin in treating pain; U.S. Pat. No. 6,127,418 discloses the use of pregabalin in treating gastrointestinal damage; and U.S. Pat. Nos. 5,599,973; 5,608,090; 5,684,189; 5,710,304; 5,616,793; 5,629,447; 5,637,767; 5,840,956; 6,046,353; and 6,028,214 disclose processes for preparing pregabalin as well an intermediate used in these processes. All of the aforementioned United States Patents are incorporated herein by reference.

U.S. Pat. No. 4,024,175 discloses the administration of gabapentin enterally or parenterally within wide dosage ranges in liquid and solid form. Subsequently, it was disclosed in U.S. Pat. No. 6,054,482, which is herein incorporated by reference, that gabapentin was converted to a lactam, i.e., 2-azaspiro[4.5]decan-3-one:

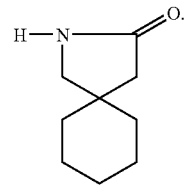

Furthermore, lactam formation unexpectedly occurred in the solid phase and under dry storage conditions. Since the gabapentin lactam displayed a certain toxicity, levels of this compound must be reduced to a minimum for reasons of safety. In further investigations, it was confirmed that liquid formulations of gabapentin undergo cyclization to form lactam much more readily than in the solid state. Additionally, it was discovered that gabapentin has a very bitter taste. Finally, there is a need to administer high doses of gabapentin in the treatment of certain diseases. In some cases, doses of up to 1500 mg per day are given to patients.

In view of the above issues, pharmaceutical compositions of gabapentin have been limited to solid dosage forms, such as capsules and tablets.

Pregabalin, similar to gabapentin, also is prone to cyclization to a lactam, i.e., 4-isobutyl-pyrrolidin-2-one:

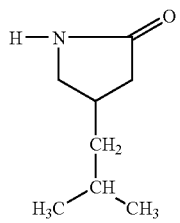

Thus, there is a need for a liquid pharmaceutical composition of GABA analogs. In particular, liquid formulations of gabapentin and pregabalin would be desirable for the treatment of small children and elderly patients, since these patient groups require doses of gabapentin or pregabalin which are easy to swallow and which can be individually dosed.

The object of the present invention is a liquid pharmaceutical composition which is amenable to high concentrations of a GABA analog, is stable, has low levels of lactam, and has an agreeable taste.

We have surprisingly and unexpectedly found that a GABA analog can be formulated in a stable liquid pharmaceutical composition having low levels of the GABA analog lactam with a pH of about 5.5 to about 7.0 containing at least one polyhydric alcohol. Additionally, the present composition has an agreeable taste.

SUMMARY OF THE INVENTION

Accordingly, a first aspect of the present invention is a liquid pharmaceutical composition of a GABA analog comprising at least one polyhydric alcohol containing 2 to 6 carbon atoms having a pH of about 5.5 to about 7.0.

A second aspect of the present invention is a method for preparing a liquid pharmaceutical composition of a GABA analog comprising:
Step (1) adding a polyhydric alcohol containing 2 to 6 carbon atoms to water;
Step (2) adding a GABA analog to the solution from Step (1); and
Step (3) optionally adjusting the pH of the composition to about 5.5 to about 7.0 to afford the liquid pharmaceutical composition.

A third aspect of the present invention is a two-component liquid pharmaceutical composition of a GABA analog comprising:
(a) a first component comprising a powder mixture of a GABA analog and a solid polyhydric alcohol;
(b) a second component comprising a liquid base wherein the powder component from (a) is added to the liquid base from (b) to afford a liquid pharmaceutical composition.

A fourth aspect of the present invention is a method for preparing a two-component liquid pharmaceutical composition of a GABA analog comprising:
Step (1) mixing a GABA analog with a solid polyhydric alcohol to afford a powder mixture;
Step (2) mixing a polyhydric alcohol with a sweetener and a flavor in water to afford a liquid base; and
Step (3) adding the powder mixture to the liquid base to afford the liquid pharmaceutical composition.

A fifth aspect of the present invention is a liquid pharmaceutical composition of a GABA analog having less than 0.5% by weight of its corresponding lactam.

A sixth aspect of the present invention is a method of using a liquid pharmaceutical composition of a GABA analog to treat subjects, including human subjects, suffering from cerebral diseases, including epilepsy, faintness attacks, hypokinesia and cranial traumas, neurodegenerative disorders, depression, mania and bipolar disorders, anxiety, panic, inflammation, renal colic, insomnia, gastrointestinal damage, incontinence, pain, including neuropathic pain, muscular pain, skeletal pain, and migraine.

DETAILED DESCRIPTION OF THE INVENTION

The term "polyhydric alcohol" refers to an alkyl or aliphatic alcohol containing from 2 to 6 carbon atoms and 2 to 6 hydroxyl groups, such as, for example, glycerol, xylitol, sorbitol, mannitol, and the like.

The term "GABA analog" refers to a compound derived from or based upon the structure of gamma-aminobutyric acid, such as, for example, gabapentin, pregabalin, and the like. Other GABA analogs that can be employed in the liquid pharmaceutical compositions of this invention are those referred to in Great Britian provisional patent application 0125807.8, which was filed on Oct. 26, 2001, Great Britian provisional patent application 0109635.3, which was filed on Apr. 19, 2001, and the corresponding PCT patent application that claims priority from the two foregoing provisional applications and which was filed in April of 2002. The foregoing applications are incorporated herein by reference in their entirties. Examples of GABA analogs that are referred to in the foregoing references are set forth below.

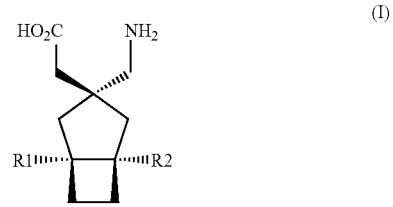

(I)

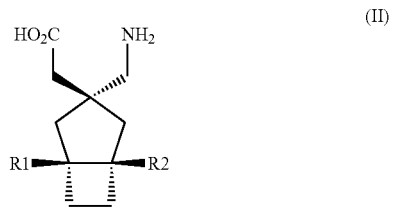

(II)

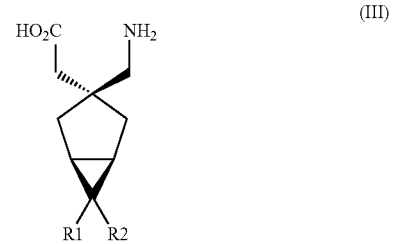

(III)

-continued
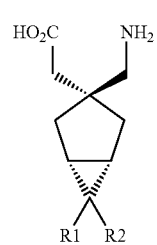
(IV)
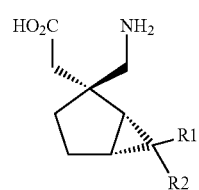
(V)
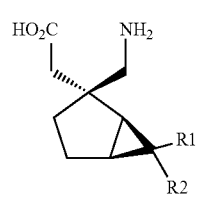
(VI)
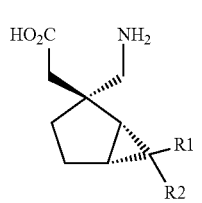
(VII)
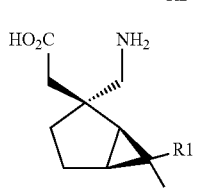
(VIII)
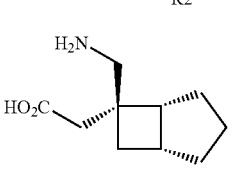
(IX)
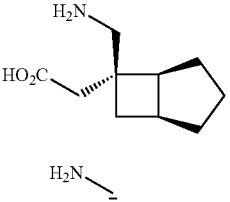
(X)
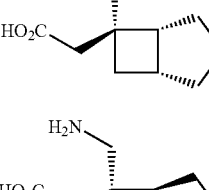
(XI)
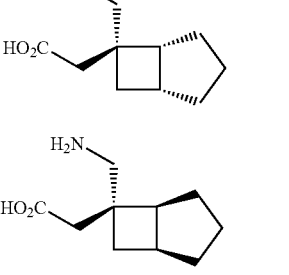
(XII)
-continued
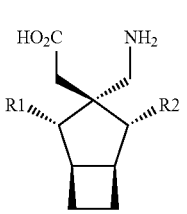
(XIII)
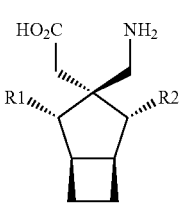
(XIV)
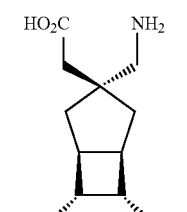
(XV)
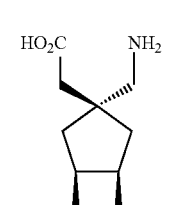
(XVI)
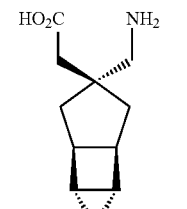
(XVII)
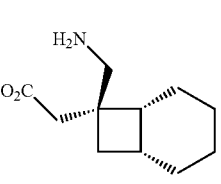
XVIII
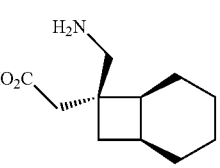
XIX

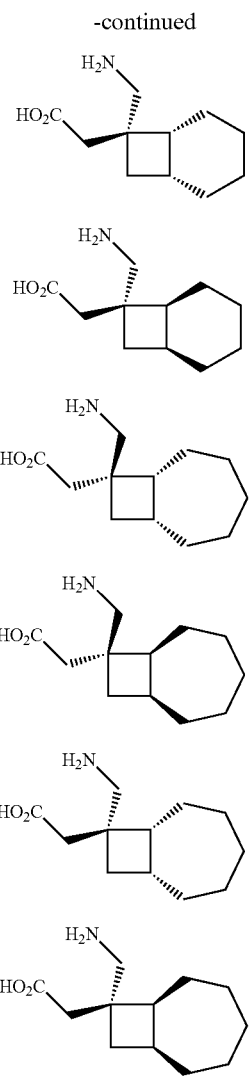

wherein R¹ and R² are each independently selected from H, straight or branched alkyl of 1-6 carbon atoms, cycloalkyl of from 3-6 carbon atoms, phenyl and benzyl, subject to the proviso that, except in the case of a tricyclooctane compound of formula (XVII), R¹ and R² are not simultaneously hydrogen.

Suitable compounds (including salts, solvates and prodrugs thereof) are:

((1R,5S)-3-Aminomethyl-1,5-dimethyl-bicyclo[3.2.0]hept-3-yl)-acetic acid;
((1S,5R)-3-Aminomethyl-1,5-dimethyl-bicyclo[3.2.0]hept-3-yl)-acetic acid;
((1R,5S)-3-Aminomethyl-6,6-dimethyl-bicyclo[3.1.0]hex-3-yl)-acetic acid;
((1S,5R)-3-Aminomethyl-6,6-dimethyl-bicyclo[3.1.0]hex-3-yl)-acetic acid;
((1S,2S,5R)-2-Aminomethyl-6,6-dimethyl-bicyclo[3.1.0]hex-2-yl)-acetic acid;
((1R,2S,5S)-2-Aminomethyl-6,6-dimethyl-bicyclo[3.1.0]hex-2-yl)-acetic acid;
((1S,2R,5R)-2-Aminomethyl-6,6-dimethyl-bicyclo[3.1.0]hex-2-yl)-acetic acid;
((1R,2R,5S)-2-Aminomethyl-6,6-dimethyl-bicyclo[3.1.0]hex-2-yl)-acetic acid;
((1R,5R,6S)-6-Aminomethyl-bicyclo[3.2.0]hept-6-yl)-acetic acid;
((1S,5S,6S)-6-Aminomethyl-bicyclo[3.2.0]hept-6-yl)-acetic acid;
((1R,5R,6R)-6-Aminomethyl-bicyclo[3.2.0]hept-6-yl)-acetic acid;
((1S,5S,6R)-6-Aminomethyl-bicyclo[3.2.0]hept-6-yl)-acetic acid;
cis-((1S,2R,4S,5R)-3-Aminomethyl-2,4-dimethyl-bicyclo[3.2.0]hept-3-yl)-acetic acid;
trans-((1S,2R,4S,5R)-3-Aminomethyl-2,4-dimethyl-bicyclo[3.2.0]hept-3yl)-acetic acid;
((1S,5R,6S,7R)-3-Aminomethyl-6,7-dimethyl-bicyclo[3.2.0]hept-3-yl)-acetic acid;
((1S,5R,6R,7S)-3-Aminomethyl-6,7-dimethyl-bicyclo[3.2.0]hept-3-yl)-acetic acid;
((1R,2S,5S)-7-Aminomethyl-3,3-dimethyl-tricyclo[3.3.0.0]oct-7-yl)-acetic acid;
((1R,6R,7S)-7-Aminomethyl-bicyclo[4.2.0]oct-7-yl)-acetic acid;
((1S,6S,7S)-7-Aminomethyl-bicyclo[4.2.0]oct-7-yl)-acetic acid;
((1R,6R,7R)-7-Aminomethyl-bicyclo[4.2.0]oct-7-yl)-acetic acid;
((1S,6S,7R)-7-Aminomethyl-bicyclo[4.2.0]oct-7-yl)-acetic acid;
((1R,7R,8S)-8-Aminomethyl-bicyclo[5.2.0]non-8-yl)-acetic acid;
((1S,7S,8S)-8-Aminomethyl-bicyclo[5.2.0]non-8-yl)-acetic acid;
((1S,7R,8R)-8-Aminomethyl-bicyclo[5.2.0]non-8-yl)-acetic acid;
((1S,7S,8R)-8-Aminomethyl-bicyclo[5.2.0]non-8-yl)-acetic acid.
[(1R,5R,6S)-6-(Aminomethyl)bicyclo[3.2.0]hept-6-yl]acetic acid;
[(1 S,5S,6R)-6-(Aminomethyl)bicyclo[3.2.0]hept-6-yl]acetic acid;
(1RS,5RS,6RS)-6-(Aminomethyl)bicyclo[3.2.0]hept-6-yl]acetic acid; and
[(1RS,6RS,7SR)-7-(Aminomethyl)bicyclo[4.2.0]oct-7-yl]acetic acid.

The liquid pharmaceutical compositions of the present invention comprise a GABA analog, such as, for example, gabapentin, pregabalin, and the like.

Gabapentin may readily be prepared as described in U.S. Pat. Nos. 5,132,451; 5,319,135; 5,362,883; 5,693,845; 5,091,567; and 5,068,413.

Pregabalin may readily be prepared as described in U.S. Pat. Nos. 5,563,175; 5,599,973; 5,608,090; 5,684,189; 5,710,304; 5,616,793; 5,629,447; 5,637,767; 5,840,956; 6,046,353; and 6,028,214.

In preparing liquid pharmaceutical compositions of the compounds of the present invention, pharmaceutically acceptable carriers are solids and liquids.

Liquid form preparations include solutions, suspensions and emulsions, for example, water or certain glycol solutions. For parenteral injections, liquid preparations can be formulated in solution in aqueous polyethylene glycol solutions.

Aqueous solutions suitable for oral use can be prepared by dissolving the active component in water and adding suitable colorants, flavors, and stabilizing and thickening agents as desired.

Aqueous suspensions suitable for oral use can be made by dispersing the finely divided active component in water with viscous material, such as, natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In the liquid pharmaceutical compositions of the present invention, it was found that if the formulation is buffered to a pH of about 5.5 to about 7.0 undesired lactam formation can be substantially avoided. However, this limits the use of certain adjuvants or carriers that can be used, such as, for example, taste-correcting acids or preservatives. Preservatives especially suited for oral compositions usually display their optimum antimicrobial activity in the acid range. Furthermore, the solubility of the usual preservatives, such as a paraben, sorbic acid, or benzoic acid decreases at low storage temperatures required for the liquid compositions of the present invention. Thus, precipitations and/or insufficient antimicrobial activity due to low concentration of the preservative at these low temperatures is to be expected. Salts of the usual preservatives have better solubility, but as a rule their antimicrobial activity is too weak.

In the development of the liquid pharmaceutical compositions of the present invention, it was shown that theoretically most alcohols possess a preserving and stabilizing action in aqueous solution. However, certain alcohols had undesirable properties and were not useful in the present pharmaceutical compositions. For example, ethyl alcohol is not desirable for pediatric formulations, propylene glycol and benzyl alcohol have an unpleasant taste, and chlorobutanol is not sufficiently stable at a pH of about 5.5 to about 7.0.

Surprisingly and unexpectedly, it was found that polyhydric alcohols containing 2 to 6 carbon atoms, preferably 3 to 6 carbon atoms, such as, for example, glycerol, xylitol, sorbitol, mannitol, and the like can be used as adjuvants for oral liquid gabapentin and pregabalin compositions. Preferably, glycerol and/or xylitol are used in the liquid compositions of the first aspect of the present invention. These adjuvants can be used in high concentration in the desired pH range of about 5.5 to about 7.0. Preferably, between a pH of about 6.0 to about 7.0. They not only act as preservatives and have a stabilizing effect on the active components, but they also substantially mask the bitter taste of the active components as a result of their sweet taste and additionally are noncariogenic. Thus, the use of one or more polyhydric alcohols allows the preparation of acceptably tasting syrups of a GABA analog especially gabapentin or pregabalin which, when cooled to refrigeration temperatures of about 2° to about 10° C., have a storage stability of at least 2 years. The polyhydric alcohols may be used in a concentration range of about 25% to about 75% (weight/volume, w/v), preferably about 30% to 75% (w/v) and most preferably about 40% to about 75% (w/v). In general, it is not necessary to add additional preservatives to the liquid compositions of the present invention. However, the addition of another preservative may be advantageous (for example, in the case of sterile-filled syrups when the container is used for multiple doses to prevent contamination of the container). In the case of a sterile-filled syrup, care must be taken in choosing an additional preservative that can be used in the desired pH range (about 5.5 to about 7.0) that does not interact with the active components and does not accelerate lactam formation. We have found that benzethonium chloride can be used as an additional preservative.

Additionally, flavor improvers can be added to the liquid compositions of the present invention to enhance the taste masking action of the polyhydric alcohols. However, only adjuvants which do not contain a reactive aldehyde or keto functionality can be used, since these functionalities react with the active components. Furthermore, the flavor improvers must not alter the desired pH range of about 5.5 to about 7.0. For example, fruity compositions have proved to be especially effective, such as, for example, aniseed, strawberry and peppermint or aniseed, huckleberry, and peppermint, and the like.

A storage temperature of about 2° C. to about 10° C., preferably about 2° C. to about 8° C. and more preferably about 4° C. to about 7° C. is required to ensure the stability of the active components and the taste of the liquid composition.

Furthermore, a liquid pharmaceutical composition of a GABA analog contains less than 0.5% (weight/weight, w/w) of the GABA analog lactam, preferably 0.4% (w/w) of lactam after storage at about 2° C. to about 10° C., preferably about 2° C. to about 8° C. for 18 months to 2 years, preferably 18 months.

The syrup-like pharmaceutical compositions of the present invention can be filled into single or multiple dose containers. For example, single dose containers can be a double sachet of coated aluminum foil which contains two half doses. An example of multiple-dose containers are glass or plastic bottles, preferably with childproof closures. The multiple dose container is variable in dosage volume and can be provided with an appropriate dosage aid, such as, a measurement beaker, measurement pipette, and the like.

Another aspect of the present invention is a two-component liquid pharmaceutical composition of a GABA analog such as, for example, gabapentin, pregabalin and the like. The composition comprises a first component comprising a powder mixture of a GABA analog and a solid polyhydric alcohol, such as, for example, sorbitol, xylitol, mannitol, and the like, preferably sorbitol, and a second component comprising a liquid syrup base containing a polyhydric alcohol, such as, for example, glycerol and the like, and one or more flavoring agents, such as, for example, artificial menthol flavor, artificial aniseed flavor, artificial blueberry flavor, and sugar and water. The liquid pharmaceutical composition is prepared by dissolving the powder blend into the syrup vehicle at the time the product is dispensed to the patient. The liquid composition once prepared should be stored at about 2° C. to about 10° C., preferably about 2° C. to about 8° C., and more preferably about 4° C. to about 7° C. However, the liquid composition may be stored at room temperature for about 2 months without exceeding undesired levels of lactam as previously described.

Dosages of gabapentin and pregabalin are well-known in the art, and the skilled practitioner will readily be able to determine the dosage amount required for a subject based upon weight and medical history.

In general, dosages of gabapentin and pregabalin are disclosed in the aforementioned United States Patents. In particular, dosages of gabapentin are disclosed in U.S. Pat. Nos. 4,024,175; 4,087,544; and 6,054,482 and pregabalin in U.S. Pat. No. 5,563,175.

The following nonlimiting examples illustrate the inventors' preferred methods for preparing and using the liquid pharmaceutical compositions of the present invention.

General Process for Preparing a Liquid Composition of Gabapentin

Water and glycerol are heated to 40° C. to 50° C., and xylitol is added with stirring. An endothermic reaction results from the dissolution of the xylitol, and the solution is cooled. After the xylitol is dissolved, the solution is cooled to 30° C. to 40° C., and gabapentin is added with stirring. After the gabapentin is completely dissolved, the flavor is added with stirring at 25° C. to 30° C. The homogeneous solution is adjusted to a pH of 5.5 to 7.0, with an acid, such as, 0.1N hydrochloric acid (HCl), or base such as 0.1N sodium hydroxide (NaOH), and filtered.

Using the above general procedure, liquid compositions of pregabalin may be prepared.

Table 1 contains representative liquid compositions of gabapentin.

TABLE 1

Liquid Composition of Gabapentin

|  | Example 1[a] | Example 2 | Example 3 | Example 4 |
|---|---|---|---|---|
| Gabapentin | 2.000 | 5.000 | 5.000 | 5.000 |
| Xylitol | 20.000 | 30.000 | 30.000 | 29.940 |
| Strawberry/anise flavor | 1.000 | — | — | 1.000 |
| Huckleberry/anise flavor | — | 1.000 | 1.000 | — |
| Glycerol 95% | 50.000 | 40.000 | 30.000 | 43.790 |
| Hydrochloric acid, 0.1 N | — | 7.720 | — | — |
| Sodium hydroxide, 0.1 N | — | — | 0.770 | — |
| Purified water | 27.000 | 16.280 | 33.230 | 20.27 |
| pH value | 6.2 | 5.5 | 7.0 | 6.5 |

[a]Amounts are in grams per 100 mL.

General Process for Preparing a Two-Component Liquid Composition of Gabapentin

Step [A] Powder Blend

Gabapentin or gabapentin monohydrate (U.S. Pat. No. 4,894,476) is blended with sorbitol.

Step [B] Syrup Base

A sorbitol solution, glycerol, granular sugar, menthol flavor, artificial aniseed flavor, and artificial blueberry flavor are dissolved in distilled water.

Step [C] Final Syrup

The syrup is prepared by dissolving the powder blend from Step [A] into the syrup base from Step [B]. The powder blend is stored in aluminum pouches and the syrup base is stored in a glass bottle at room temperature. After preparing the syrup extemporaneously, the syrup is stored under refrigeration.

Using the above general procedure, two-component liquid compositions of pregabalin may be prepared.

Table 2 contains a representative liquid composition of gabapentin.

TABLE 2

Two-Component Liquid Composition of Gabapentin

| Powder Blend | |
|---|---|
| Gabapentin Monohydrate (Equivalent to 9.00 g gabapentin) | 9.90 g |
| Sorbitol | 22.50 g |
| Syrup Base | |
| Sorbitol Solution | 225.00 g |
| Glycerin, USP | 180.00 g |
| Sugar, Granular | 45.00 g |
| Artificial Menthol Flavor[a] | 56.25 mg |
| Artificial Aniseed Flavor[b] | 22.50 mg |
| Artificial Blueberry Flavor | 4.275 g |
| Water, Distilled | qs[c] to 450 mL |

[a]Actually 2.5% solution of menthol in alcohol is weighed.
[b]Actually 2.5% solution of aniseed in water is weighed.
[c]Quantity sufficient

What is claimed is:

1. A liquid pharmaceutical composition comprising: an amino acid selected from the group consisting of gabapentin and pregabalin; one or more polyhydric alcohols, each containing 2 to 6 carbon atoms; and water; wherein the one or more polyhydric alcohols comprises about 25 g to about 75 g per 100 mL of the composition and the composition has a pH of about 5.5 to 7.0.

2. The composition according to claim 1, wherein the one or more polyhydric alcohols each contains 3 to 5 carbon atoms.

3. The composition according to claim 1, wherein the one or more polyhydric alcohols are selected from the group consisting of: glycerol, xylitol, sorbitol, mannitol, and mixtures thereof, and wherein the one or more polyhydric alcohols comprises about 40 g to about 75 g per 100 mL of the composition.

4. The composition according to claim 1, comprising one or both of: a preservative and a flavor improver, wherein the flavor improver does not contain an aldehyde or keto functionality.

5. The composition according to claim 1 wherein the amino acid is gabapentin.

6. The composition according to claim 1 wherein the composition has less than 0.5% by weight of the corresponding lactam of the amino acid.

7. The composition of claim 1, wherein the amino acid is gabapentin, and the composition contains less than 0.5% weight/weight of gabapentin lactam after storage at 2° C. to 10° C. for 18 months to 2 years.

8. The composition of claim 1, wherein the amino acid is gabapentin, the one or more polyhydric alcohols is selected from the group consisting of xylitol, glycerol and mixtures thereof.

* * * * *